United States Patent [19]
Chambers et al.

[11] 3,952,030
[45] Apr. 20, 1976

[54] SELENIUM-75 STEROIDS

[75] Inventors: Virginia Edith May Chambers; Anthony Leonard Mark Riley, both of Amersham, England

[73] Assignee: The Radiochemical Centre Ltd., Amersham, England

[22] Filed: Dec. 20, 1973

[21] Appl. No.: 426,695

[30] Foreign Application Priority Data
Dec. 27, 1972 United Kingdom............... 59690/72

[52] U.S. Cl..................... 260/397.4; 260/239.55 A; 260/239.55 R; 260/397.2; 260/397.3; 260/397.45; 424/2
[51] Int. Cl.²....................... C07J 1/00; G01T 1/00; C07J 5/00; C07J 9/00
[58] Field of Search.......... 260/239.55 R, 239.55 A, 260/397.2, 397.3, 397.4, 397.45, 397.45 I

[56] References Cited
FOREIGN PATENTS OR APPLICATIONS
811,867   8/1959   United Kingdom............ 260/397.45

*Primary Examiner*—Ethel G. Love
*Attorney, Agent, or Firm*—Wenderoth, Lind & Ponack

[57] ABSTRACT

Novel dimeric and monomeric selenium-75 derivatives of steroids are made by reacting a keto steroid with selenium-75 dioxide or selenious acid-Se75. The resulting diselenide dimers can be converted into monomeric compounds by the use of a cleaving reagent followed by an alkylating agent. The compounds are useful in saturation analyses such as radioimmunoassays.

10 Claims, No Drawings

SELENIUM-75 STEROIDS

This invention relates in broad terms to selenium-75 derivatives of steroids, and particularly to two groups of novel selenium-75 derivatives of steroids; to the preparation of such novel derivatives; and to the use of both groups of compounds for saturation analysis. Derivatives for use in such analyses contain the γ-emitting Se75 isotope.

The preparation of steroids containing Se75 has not previously been described in the literature, neither has the idea of using Se75 labelled compounds for saturation analysis.

cortisol
testosterone
progesterone
aldosterone
cholesterone
deoxycorticosterone
3-dehydrodigitoxigenin
3-dehydrodigoxigenin The compound preferably, but not essentially, has a double bond in the 4-5 position of each steroid molecule. Thus in the specific case of the compound derived from cortisol-21-acetate the structural formula is believed to be:

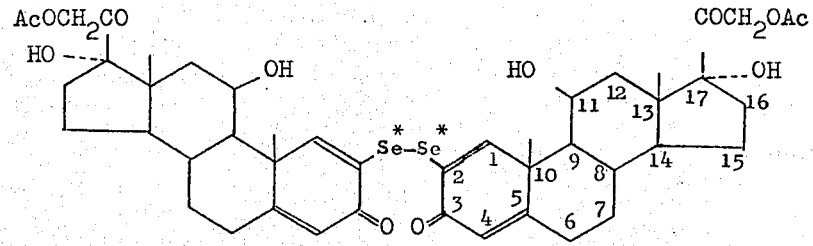

This invention provides, in one aspect, a series of novel dimeric selenium derivatives of steroids having the following characteristics:

a. each compound is obtainable by reacting a 3-keto, or a 6-keto, or a 7-keto, or a 17-keto steroid, preferably a $\Delta^4$,3-keto steroid, with selenium-75 dioxide or selenious acid-Se75. The reaction is preferably effected in an organic solvent for the steroid reactant which is unattacked by the selenium-75 reactant under the reaction conditions employed, and in which the basic steroid skeleton is stable. Suitable organic solvents include ethers, e.g. dioxan, organic acids, e.g. acetic acid, and benzene although it is likely that a wide range of solvents may be used. The reaction is generally carried out at an elevated temperature, e.g. from 80°C to 140°C, conveniently the reflux temperature of the organic solvent.

b. Selenium-75 may be used in admixture with stable isotopes of selenium at any desired specific activity. Compounds obtained using selenium-75 have considerable utility in saturation analysis. The γ-emitting Se75 isotope is the only selenium isotope suitable for saturation analysis where high specific activities and a reasonable half-life are required (Se75 may conveniently be obtained at specific activities of >20 Ci/mAtom).

c. The compounds are believed to be diselenide dimers of the steroid concerned. Thus, it is believed that 3-keto steroids generate 2,2'-diselenide dimers; 6-keto steroids generate 7,7'-diselenide dimers; 7-keto steroids generate 6,6'-diselenide dimers; and 17-keto steroids generate 16,16'-diselenide dimers.

Thus the compounds obtained from 3-keto steroids are believed to contain the grouping

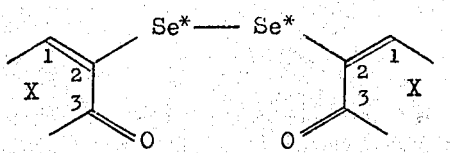

where X is the remainder of a steroid molecule, for example from

Compounds derived from 6-keto steroids are believed to contain the grouping

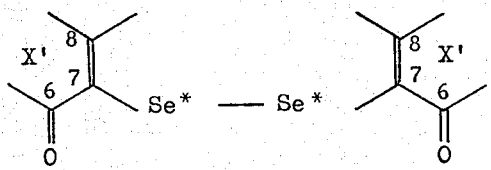

Compounds derived from 7-keto steroids are believed to contain the grouping

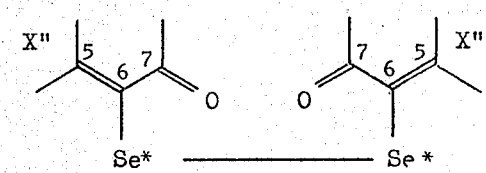

Compounds derived from 17-keto steroids are believed to contain the grouping

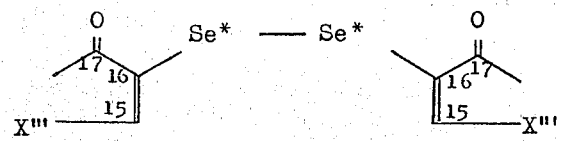

where X', X" and X''' are in each case the remainder of a steroid molecule.

Care must be taken that groups on the steroid molecule which are susceptible to selenium dioxide oxidation are suitably protected. Thus, for example, certain hydroxyl groups can be protected as esters, which may readily be hydrolysed to yield free hydroxyl groups after the introduction of selenium-75 into the molecule.

In another aspect, the invention provides a further series of novel selenium-75 derivatives of steroids having the following characteristics:

a. each compound is obtainable by splitting one of the dimeric selenium-75 derivatives hereinbefore defined, by the use of a cleaving reagent followed by an alkylating agent. Numerous ways of cleaving diselenide linkages are known (J. Org. Chem. 32 3931 and 31, 1202). These include dissolving metal reductions (e.g. sodium in anhydrous ammonia or ethanol and zinc in acid or alkali solutions), sodium ethoxide, hydrazine, hypophosphorous acid, sodium borohydride and dithiothreitol. β-Mercaptoethanol does reduce the diselenide bond, but is found to be less effective than dithiothreitol.

The use of a number of these reagents is restricted by the reactivity of the functional groups on the steroids. Of those remaining, dithiothreitol, β-mercaptoethanol, and hypophosphorous acid are considered to be the most convenient. The products which are formed when the dimeric selenium-75 derivatives are treated with cleaving agents were not isolated. Treatment of these products with an alkylating agent, for example methyl iodide, enables stable monomeric selenium-75 derivatives to be isolated. Thus, for example, yields of Se-methyl compounds from the corresponding diselenides were obtained as follows:

1. Prepared from dithiothreitol and methyl iodide

| | |
|---|---|
| 2-methylseleno-1-dehydrotestosterone-17-acetate (inactive) | 40% |
| 2-methylseleno-1-dehydrocortisol-21-acetate Se75 | 30% |

2. Prepared from hypophosphorous acid and methyl iodide

| | |
|---|---|
| 2-methylseleno-1-dehydrocortisol-21-acetate Se75 | 3% | b. The compounds are believed to be selenoalkyl derivatives of the steroid concerned. Reasons for this belief, and also for thinking that the compounds are the 2-selenoalkyl derivatives, are set out in the Examples which follow. Certain compounds in this series are believed to have the following general formulae:

From 3-keto steriods

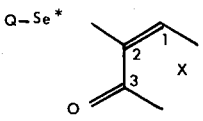

From 6-keto steriods

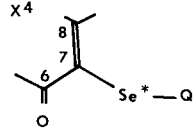

From 7-keto steriods

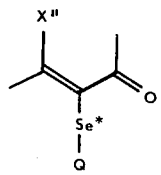

From 17-keto steriods

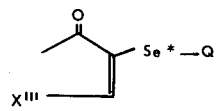

where Q is a hydrocarbon group, preferably an alkyl group, and the significance of X, X', X" and X''' is the same as in the dimeric selenium derivatives described above.

These compounds, like the dimeric selenium derivatives, are useful labelled compounds for saturation analysis, for example, for radioimmunoassays or protein binding assays. For example, using transcortin from rabbit serum as the binding agent, we have shown that bis-2,2'-(1-dehydrocortisol-21-acetate-diselenide-Se75 competes satisfactorily with cortisol enabling a suitable assay for corticosteroids to be devised. Bulk stocks of the dimeric selenium derivatives in organic solvent were shown to give useful dose-response curves even after several months storage. However, when the diselenide was stored overnight in the buffer/serum mixture no dose-response curve was obtained the next day. This was a clear disadvantage as it might be more convenient to predispense the assay tubes some time before use.

The addition to the predispensed assay of reagents which could cleave the diselenide linkage was found to be advantageous and an assay to which β-mercaptoethanol had been added still gave a satisfactory dose-response curve after 28 days storage at room temperature.

The use of the monomeric selenium derivatives as the labelled compound gave an even more sensitive assay with the added advantage of a stability of >100 days when kept as a predispensed assay.

Although the assays described in the Examples below use the dextran polymer available commercially under the Trade Name Sephadex for the separation of "free" and "bound" corticosteroids, the labelled compounds described above can also be used satisfactorily in assays using charcoal or other conventional materials for separation of "free" and "bound" corticosteroids.

The compounds find utility in analysis kits for assaying steroids, particularly keto-steroids, which kits comprise:

a. a dimeric or monomeric selenium-75 derivative of a steroid as defined above,
b. a specific reagent to react with the steroid to be assayed, and
c. a plurality of tubes for performing the assay.

The selenium-75 steroid derivatives and the specific reagent may conveniently be predispensed into the tubes and freeze-dried as described in our co-pending British Patent Application No. 58565/71. Thus, for example, in the case of the cortisol assay discussed above, the kit might be supplied with each tube containing the selenium-75 labelled cortisol, the binding protein transcortin, buffer and stabiliser, and possibly Sephadex.

The following Examples illustrate the invention.

EXAMPLE I

Preparation of selenious acid-Se75

Elementary selenium, Se75, (prepared by neutron irradiation of elementary selenium enriched in Se74) of the required specific activity, was dissolved, with warming, in concentrated nitric acid. The mixture was centrifuged and the supernatate was diluted with water. The required amount of selenious acid-Se75 could then be obtained by subdivision of the above solution.

Treatment of cortisol acetate with selenious acid-Se75

Cortisol acetate (27 mg) and glacial acetic acid (4 ml) were added to a reaction tube containing selenious acid (290 mCi; sp. activity ca 5.5 Ci/m.atom) prepared as above. The mixture was heated under reflux for 1 hour and then allowed to cool. Chloroform (10 ml) was added and the mixture was washed thoroughly with water (2 × 15 ml) and dilute aqueous sodium bicarbonate solution (2 × 15 ml). The chloroform was removed by freeze-drying to yield a pale yellow foam (ca 220 mCi). The crude mixture was purified by thin layer chromatography [SiO$_2$ eluted with EtOAc : benzene 4:6]. The required product (35 mCi) was obtained by elution of the main radioactive bond with ethyl acetate (3 × 3 ml). The product was shown to be greater than 98% radiochemically pure by thin layer chromatography. Spraying of the chromatogram with orthophosphoric acid and ultraviolet visualisation did not reveal any inactive impurities. The chromatographic properties of the product obtained in this synthesis were identical with those obtained when inactive selenium was incorporated.

EXAMPLE II

Preparation of bis-2,2'-(1-dehydrocortisol-21-acetate)-diselenide

Cortisol acetate (2 g) in glacial acetic acid (20 ml) was treated with selenium dioxide (1 g). The mixture was heated under reflux for 1 hour and then filtered before extracting with chloroform. The organic extract was washed with water and aqueous sodium bicarbonate and purified by chromatography to give (260 mg) crystalline solid, m.p. 291°–294° (from Et$_2$O:MeOH) $\lambda_{max}$ 244 258 and 304 nm; $\nu_{max}$ 1650, 1730 and 1740 cm$^{-1}$. X-ray spectrofluorescence proved the presence of selenium. This product had chromatographic properties identical with those observed for the product from Example I.

EXAMPLE III

Treatment of testosterone acetate with SeO$_2$

Testosterone acetate (1 g), selenium dioxide (380 mg) and glacial acetic acid (10 ml) were heated under reflux for 1 hour. The mixture was diluted with chloroform, filtered and then washed with water and aqueous sodium bicarbonate. The organic extract was evaporated to dryness and then partially purified by filtration of a benzene solution through a column of alumina. Further purification of the product by preparative layer chromatography [EtOAc:benzene (4:6)] yielded a white solid (ca 500 mg); m.p. 155°–160° (from acetone), molecular weight 805 (with a standard deviation of 4% by vapour pressure osmomemtry on a chloroform solution), $\lambda_{max}$ 244, 258 and 304 nm, $\nu_{max}$ 1605, 1630, 1655, 1735 cm$^{-1}$.

The presence of selenium was confirmed by X-ray spectrofluorescence.

Hydrolysis of the product in alkaline aqueous ethanol gave the corresponding $\Delta^1$-testosterone derivative.

A nuclear magnetic resonance spectrum (for CDCl$_3$ solution) showed the presence of methyl signals at $\gamma 9.20$ (18-H), 8.83 (19-H) and 7.98 (-OCCH$_3$-acetate methyl). The presence of these as the only methyl signals and their intensity ratio of 1:1:1 (a) proves no substitution can have occurred on the 19-methyl group and therefore no 6$\beta$-19-seleno bridge was present and (b) suggests the molecule is symmetrical. The only other significant signals in the n.m.r. spectrum were two singlet olefinic signals at $\gamma$ 3.9 and 2.88. These indicate the presence of two trisubstituted olefins one of which (with absorption at $\gamma$ 3.9) is due to H-4 by comparison with spectra of testosterone acetate and 1-dehydrotestosterone acetate. There are two obvious positions for the second double bonds, namely the $\Delta^1$ and $\Delta^6$ positions.

From the ultraviolet spectrum ($\lambda_{max}$ 244, 258, 304 nm), the possibility of a $\Delta^6$ bond was eliminated ($\lambda_{max}$ $\Delta^{4,6}$-3CO at ca 280 nm)[5]. This leaves only two positions at which the dimeric linkage could occur; these are at positions 1 and 2.

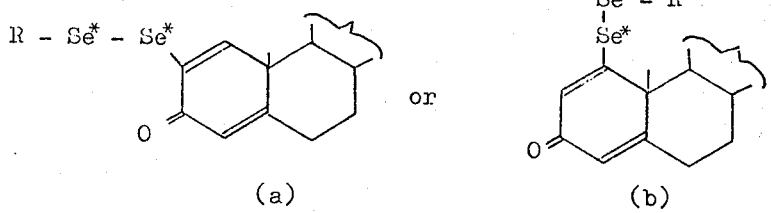

From the low field position of the second olefinic signal it seems most likely that substitution has occured at position 2.

Bis-2,2'-(1-dehydrotestosterone)-diselenide-Se75 can be obtained by the method described above using selenium-75 dioxide.

Similar spectroscopic and molecular weight evidence to that given in this Example was obtained for the diselenide obtained from cortisol acetate (Example II).

EXAMPLE IV

Treatment of a mixture of cortisol acetate and testosterone acetate with selenium dioxide Cortisol acetate (120 mg; 0.4 mmole), testosterone acetate (100 mg; 0.37 mmole) and selenium dioxide (120 mg) in glacial acetic acid (15 ml) were heated under reflux for 1 hour. The mixture was diluted with CHCl$_3$, filtered and then washed with water and aqueous sodium bicarbonate. Evaporation of the solvent gave an orange foam which was purified by preparative layer chromatography SiO$_2$, eluted with EtOAc:benzene (4:6). At least six bands were obtained under ultraviolet light. Removal of the band of Rf).49 yielded a white solid which was shown by spectroscopy to be a compound containing $\Delta^1$ - cortisol acetate and $\Delta^1$ - testosterone acetate, probably linked by a diselenide bridge. The use of selenium-75 dioxide gives rise to the corresponding selenium-75 compound.

EXAMPLE V

Preparation of bis-2,2'-(1-dehydrocorticosterone-21-acetate)-diselenide-Se75

Corticosterone-21-acetate (30 mg) in glacial acetic acid was treated at reflux for 1 hour with selenious acid-Se75 (240 mCi ca 5 Ci/m atom) as described above (Example I). Purification by thin layer chromatography yielded the required product (42.5 mCi).

Treatment of this product (2.5 mCi) in ethanol (0.5 ml) with dilute aqueous potassium carbonate (0.25 ml) gave bis-2,2'(1-dehydrocorticosterone)-diselenide-Se75 (1:1 mCi) after chromatographic purification.

EXAMPLE VI

Incorporation of selenium into 6-oxo oestriol triacetate

6-Oxo oestriol triacetate (6 mg) in glacial acetic acid was treated with selenium dioxide (containing $^{75}SeO_2$, 0.25 mCi) as described in Example II. Extraction with chloroform as usual gave 80% yield of radioactivity in the organic phase. Tlc ($CHCl_3$:acetone 98:2) showed that three active products had been formed.

EXAMPLE VII

Treatment of 3$\beta$-acetoxy-androst-5-en-17-one

The steroid (33 mg) in glacial acetic acid was treated with selenium dioxide (11 mg) (containing $^{75}SeO_2$, 2 mCi) as previously. Extraction with chloroform yielded 85% radioactivity in the organic phase. Tlc showed a complex mixture of radioactive steroidal products.

EXAMPLE VIII

Treatment of 3$\beta$-acetoxy-5$\alpha$-cholestan-7-one

3$\beta$-Acetoxy-5$\alpha$-cholestan-7-one (10 mg) was treated with selenium dioxide (4 mg) (containing $^{75}SeO_2$, 2 mCi) as described above. Partition between chloroform and water yielded 65% radioactivity in the organic phase. Preparative layer chromatography [$SiO_2$, $CHCl_3$:acetone (98:2)] gave one major active component, which was removed and found to be stable over one month.

EXAMPLE IX

Preparation of 2-methylseleno-1-dehydrocortisol-21-acetate-Se75 i. Using dithiothreitol as cleaving agent

Bis-2,2'-(1-dehydrocortisol-21-acetate)-diselenide-Se75 (1.18 mCi; sp. activity 20 mCi/m atom) was added to tris buffer (pH 7.5; 4 ml). A precipitate formed. Addition of dithiothreitol (5.7 mg) in ethanol (1 ml) caused the precipitate to dissolve to give a yellow solution which became orange on warming gently for several minutes. Methyl iodide (0.25 ml) was added and the solution was kept at 30°–40° for 25 minutes. After being partitioned between water and chloroform the reaction mixture was purified by preparative layer chromatography [$SiO_2$, eluted with EtOAc:benzene (4:6)]. The fastest running radioactive band was extracted with ethyl acetate to give a 30% yield (0.39 mCi) of the required product.

ii. Using hypophosphorous acid

The process was repeated but omitting the tris buffer and substituting an equimolar proportion of hypophosphorous acid for the dithiothreitol. Purification of the reaction mixture as previously described yielded 40% (0.52 mCi) of the desired product.

iii. Using $\beta$-Mercaptoethanol

A solution of the diselenide (1.65 mCi; sp. activity 5.5 mCi/mA) in ethanol (1 ml) was purged with nitrogen. $\beta$-Mercaptoethanol (0.25 ml) was added and the solution was warmed for a short time before the addition of methyl iodide (0.25 ml). After 30 minutes at room temperature, the reaction mixture was concentrated in vacuo and then extracted as described above to give 0.05 mCi of the required material.

The experiments described in Example IX were repeated but using inactive bis-2,2'-(1-dehydrocortisol-21-acetate)-diselenide, inactive methyl iodide and S35 labelled dithiothreitol or 2-mercaptoethanol. A product identical with that obtained in Example IX resulted. The absence of any activity in the product proved the absence of sulphur in the alkyl selenosteroid.

The presence of the alkyl group was proven by use of methyl iodide-C14 together with inactive steroidal diselenide and cleaving agents. Additional evidence for the presence of the alkyl group was obtained from the n.m.r. spectrum. Inactive 2-methylseleno-1-dehydrocortisol-21-acetate (in $DMSOd_6/D_2O$) had signals at $\tau$ 9.2 and 8.6 (C-18 and C-19 methyls), 7.90 (Se-Me), 7.94 (21-OAc), 4.00 (4-H) and 2.95 (1-H).

EXAMPLE X

Preparation of 2-methylseleno-1-dehydrotestosterone acetate

Bis-2,2'-(1-dehydrotestosterone acetate)-diselenide (44.5 mg) in ethanol (5 ml) was purged with nitrogen. The pH was adjusted to 7.5 and a solution of dithiothreitol (25.6 mg) in ethanol (10 ml) was added. The mixture was warmed gently to achieve solution. Methyl iodide (1.25 ml) was added and the mixture was kept at room temperature for 30 minutes before extraction with chloroform as described above. Purification of the reaction mixture by chromatography gave the desired product (20 mg). The corresponding selenium-75 compound can be made starting from bis-2,2'-(1-dehydrotestosterone acetate)-diselenide-Se75.

EXAMPLE XI

Incorporation of Selenium into 3-dehydrodigitoxigenin

3-Dehydrodigitoxigenin in glacial acetic acid was treated with selenium dioxide as described in Example II. The product was extracted with chloroform which was washed with water and aqueous sodium bicarbonate and then evaporated to give an orange oil. Treatment of the oil, in ethanol, with dithiothreitol and methyl iodide (as described in Example IX) gave crude product. Purification by preparative layer chromatography [$SiO_2$, eluted with benzene:ethyl acetate (1:1)] gave a white solid, m.p. ca 170° (decomp.); $V_{max}$ 1640 (unsaturated 6-membered ring ketone), 1740 and 1770 (lactone); $\lambda_{max}$ 250 and 325 m$\mu$. An n.m.r. spectrum (for $CDCl_3$ solution) confirmed that the selenium was in the expected environment with signals at $\tau$ 7-92 (3H-SeMe) and low field olefinic signals indicated the presence of a 1-2 double bond.

The incorporation of selenium was confirmed by the preparation of the same product using low specific activity Se-75.

EXAMPLE XII

Treatment of cholest-4-en-3-one with selenium dioxide

Cholest-4-en-3-one (1 g) and selenium dioxide (500 mg) in glacial acetic acid (20 ml) were heated under reflux for 1 hour. The mixture was extracted as described for previous examples and applied to six SiO$_2$ preparative layer plates. Elution with benzene:ethyl acetate (1$^2$:1) gave one main UV fluorescent band which yielded ca 300 mg yellow solid after extraction with ethyl acetate. An ultraviolet spectrum $\lambda_{max}$ 304, 257, 246 m$\mu$) indicated the presence of a $\Delta^{1,4}$ diselenosteroid (see Example III).

Treatment of the product is ethanol containing tris buffer (pH 7.4) with dithiothreitol and methyl iodide gave an oil. UV ($\lambda_{max}$ 250 and 325 m$\mu$) confirmed the cleavage of the diselenide bond.

The experiment can be repeated using selenium-75 dioxide.

EXAMPLE XIII

Treatment of aldosterone diacetate with selenium dioxide (or selenious acid)

Inactive

Aldosterone diacetate (50 mg), and selenium dioxide (50 mg) in dioxane (6 ml) were heated under reflux for 1 hour. Work-up as described previously followed by preparative layer chromatography (SiO$_2$, eluted with benzene:chloroform:acetone 2:1:1) gave two UV fluorescent bands. The main band (less polar than starting material) was removed and eluted with chloroform to give a product having UV ($\lambda_{max}$ 245, 258, 305 m$\mu$). This product was treated with dithiothreitol and methyl iodide at pH 7.4 as described previously and then purified by tlc to give an oil. An ultraviolet spectrum ($\lambda_{max}$ 325 and 250 m$\mu$) suggested the cleavage of a diselenide linkage. An infrared spectrum (CHCl$_3$ solution) showed the presence of a diacetate (V$_{max}$ 1750 cm$^{-1}$) and unsaturated six membered ring ketone (V$_{max}$ 1655 cm$^{-1}$).

Low specific activity Se-75

The above preparation was repeated on a 10 mg scale using selenium dioxide (10 mg, 2mCi).

Analysis of the final product mixture by thin layer chromatography showed the main active product to be of the same R$_f$ as the product from the inactive preparation above.

EXAMPLE XIV

A typical assay for cortisol using Se-75 labelled bis-2,2'-(21-acetoxy-1-dehydrocortisol)-diselenide Into each glass assay tube was dispensed glycine buffer containing 1% sodium azide (pH 9.0; 5.5 ml), charcoal treated rabbit serum (50 $\mu$l), bis-2,2'-(21-acetoxy-1-dehydrocortisol)-diselenide-Se75 (2.3 ng, sp. activity ca 6 Ci/m atom), and Sephadex G25 (1 g). Standard solutions of cortisol containing 0, 2, 4, 8, 16, 32 and 64 ng/100 ml in buffer were freshly prepared and aliquots (100 $\mu$l) of each solution were added individually to each one of the above assay tubes. The tubes were capped and rotated at room temperature for 1 hour using a Blood Cell Suspension Mixer. After this time an aliquot (1 ml) of the supernatant liquid was withdrawn from each tube and counted for 300 seconds using an NE8311 gamma counter.

| Results<br>Counts — Bkdg in 300 sec | Cortisol concentration<br>Standard $\mu$g/100 ml |
|---|---|
| 34672 | 0 |
| 33573 | 0 |
| 31116 | 2 |
| 32296 | 2 |
| 31129 | 4 |
| 31389 | 4 |
| 29987 | 8 |
| 30954 | 8 |
| 29141 | 16 |
| 29356 | 16 |
| 26842 | 32 |
| 25739 | 32 |
| 23746 | 64 |
| 25895 | 64 |

EXAMPLE XV

A typical assay for cortisol - the use of $\beta$-mercaptoethanol in situ

Bis-2,2'-(21-acetoxy-1-dehydrocortisol)-diselenide-Se75 (100 ng) in ethanol (10 $\mu$l) was added with stirring to a solution of $\beta$-mercaptoethanol (20 $\mu$l) in 0.05M phosphate buffer (pH 7.4; 1 ml). The mixture was left at room temperature for 20 minutes and then was added to a solution of 0.05M of phosphate buffer (pH 7.4; 480 ml) containing sodium azide (1%) and charcoal treated rabbit serum (2 ml). After thorough mixing this solution was dispensed (in 6 ml aliquots) into glass assay tubes each containing Sephadex G25 (1 g). The tubes were capped and stored at room temperature until required, when the assay was then carried out as described above.

| Cortisol<br>Standard<br>$\mu$g/100 ml | Counts per 100 seconds<br>(corrected for background)<br>Storage time (days) | |
|---|---|---|
| | 1 | 28 |
| 2 | 12814 | 13007 |
| 2 | 13112 | 12356 |
| 4 | 13012 | 11884 |
| 8 | 12754 | 11486 |
| 8 | 12709 | 11624 |
| 16 | 11825 | 10467 |
| 16 | 11980 | 10930 |
| 32 | 10988 | 10078 |
| 32 | 10876 | 10365 |
| 64 | 9636 | 9967 |

EXAMPLE XVI

A typical assay for cortisol using 2-methylseleno-1-dehydrocortisol 21-acetate-Se75

Into each glass assay tube was dispensed 0.05M phosphate buffer containing sodium azide 1% (pH 7.4; 6 ml), charcoal treated rabbit serum (50 $\mu$l), 2-methylseleno- 1-dehydrocortisol- 21-acetate-Se75 (2.5 ng; sp. activity ca 3 Ci/m atom), and Sephadex G25 (1 g).

The assay procedure was identical with that described above. The figures given below show that an assay having a steeper dose-response curve may be performed using the methylseleno rather than the diseleno-derivative.

| Results<br>Cortisol<br>Standard $\mu$g/100 ml | Counts — BKG in 300 sec |
|---|---|
| 0 | 37447 |

-continued

| Results Cortisol Standard μg/100 ml | Counts — BKG in 300 sec |
|---|---|
| 0 | 37551 |
| 2 | 36495 |
| 2 | 36981 |
| 4 | 35381 |
| 4 | 34565 |
| 8 | 31090 |
| 8 | 32353 |
| 16 | 28011 |
| 16 | 28180 |
| 32 | 24135 |
| 32 | 24340 |
| 64 | 21601 |
| 64 | 21777 |

We claim:
1. A selenium-75 derivative of a 3-keto steroid selected from the group consisting of cortisol, testosterone, progesterone, aldosterone, cholesterone, deoxycorticosterone, 3-dehydrodigitoxigenin and 3-dehydrodigoxigenin.
2. A derivative as claimed in claim 1, containing the group

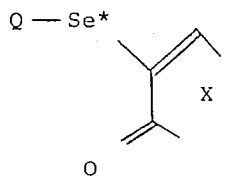

where Q is an alkyl group and X is the remainder of the 3-keto steroid molecule.
3. A derivative as claimed in claim 1, containing the group

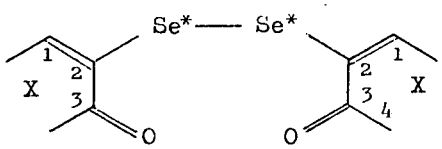

where X is the remainder of the 3-keto steroid molecule.
4. Bis-2,2'-(1-dehydrocortisol-21-acetate)-diselenide-Se75.
5. Bis-2,2'-(1-dehydrotestosterone)-diselenide-Se75.
6. Bis-2,2'-(1-dehydrocorticosterone-21-acetate)-diselenide-Se75.
7. 2-Methylseleno-1-dehydrocortisol-21-acetate-Se75.
8. 2-Methylseleno-1-dehydrotestosterone-acetate-Se75.
9. A method of making a selenium-75 derivative claimed in claim 2, which comprises reacting a 3-keto steroid selected from the group consisting of cortisol, testosterone, progesterone, aldosterone, cholesterone, deoxycorticosterone, 3-dehydrodigitoxigenin and 3-dehydrodigoxigenin with selenium-75 dioxide or selenious acid Se-75, splitting the resultant diselenide dimer with the use of a cleaving reagent selected from the group consisting of dithiothreitol, β-mercaptoethanol and hypophosphorous acid and treating the resultant product with an alkylating agent.
10. A method of making a selenium-75 derivative claimed in claim 2, which comprises
   a. reacting a 3-keto steriod selected from the group consisting of cortisol, testosterone, progesterone, aldosterone, cholesterone, deoxycorticosterone, 3-dehydrodigitoxigenin and 3-dehydrodigoxigenin with selenium-75 dioxide or selenious acid Se-75 in an organic solvent for the steroid reactant, which solvent is chemically inert to the reactants under the conditions employed, at a temperature of from 80°C to 140°C,
   b. splitting the resultant diselenide dimer with the use of a cleaving reagent selected from the group consisting of dithiothreitol, β-mercaptoethanol and hypophosphorous acid,
   c. treating the resultant product with an alkylating agent, and
   d. recovering the resultant selenium-75 steroid derivative.

* * * * *